(12) United States Patent
Jungfer et al.

(10) Patent No.: US 6,511,848 B2
(45) Date of Patent: *Jan. 28, 2003

(54) PROCESS FOR PRODUCING AND MULTIPLYING LYMPHOCYTES

(75) Inventors: Herbert Jungfer, Stabrnbert (DE); Heinrich Barchet, Bernried (DE); Winfried Albert, Eberfing (DE)

(73) Assignee: Winfried Albert, Hannover-Langenhagen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/147,134

(22) PCT Filed: Apr. 17, 1997

(86) PCT No.: PCT/EP97/01924
§ 371 (c)(1),
(2), (4) Date: Nov. 12, 1998

(87) PCT Pub. No.: WO97/39108
PCT Pub. Date: Oct. 23, 1997

(65) Prior Publication Data
US 2002/0055170 A1 May 9, 2002

(30) Foreign Application Priority Data
Apr. 17, 1996 (EP) ............................... 96105993

(51) Int. Cl.[7] ............................ C12N 5/08; C12N 5/00; C12N 5/06
(52) U.S. Cl. ................... 435/372; 435/372.3; 435/384; 435/386
(58) Field of Search ........................... 435/372.2, 372.3, 435/384, 386, 372

(56) References Cited

U.S. PATENT DOCUMENTS 5,045,454 A * 9/1991 Bertheussen ............. 435/29
5,149,701 A * 9/1992 Shafiee et al. ............ 514/291
5,354,686 A * 10/1994 Haberman ............... 435/240.2
5,521,161 A * 5/1996 Malley et al. ............. 514/45
5,660,824 A * 8/1997 Grabstein et al. .......... 424/85.2

FOREIGN PATENT DOCUMENTS

EP  0 409 655 A2  1/1991

OTHER PUBLICATIONS

Burres et al. The JOurnal of Antibiotics. Dec. 1991. vol. 44, No. 12, pp. 1331–1341.*
Guyton A. C. Textbook of Medical Physiology. 8 edition. W.B. Sauders Compant. 1993. p. 168. 375.*
Pechhold et al. Eur. J. Immunol. 1993, vol. 23, pp. 562–565.*
Kroemer G. "The Pharmacology of T Cell Apoptosis", Advances in Immunology, 1995, vol. 58, pp. 211–296.*
Cerwenka et al. The Journal of Immunology, 1996, 156, pp. 459–464.*
Blood, vol. 87, No. 1 (Jan. 1), 1996, pp 180–189, Pierson et al., "Human National Killer Cells Expansion is Regulated by Thrombospondin–Mediated Activation of Transforming Growth . . . ".
Periodicum Biologorum, vol. 92, Supp. 3, 1990, Kotnik et al., "Lymphokines and Cytokines".
Immunopharmacology and Immunotoxicology, 16(2), 179–190 (1994), Weaver et al., "The Interaction of Immunosuppressive Compounds in Tandem Stimulated Peripheral Human Lymphocytes".

* cited by examiner

*Primary Examiner*—Irene Marx
*Assistant Examiner*—Vera Afremova
(74) *Attorney, Agent, or Firm*—Arent Fox Kintner Plotkin & Kahn, PLLC

(57) ABSTRACT

A method for culturing and/or multiplying lymphocytes in cell culture medium which contains as lymphocyte growth factor and additionally, aurin tricarboxylic acid, ciclosporin, tacrolimus, and/or ascomycin.

7 Claims, 2 Drawing Sheets

PROCESS FOR PRODUCING AND MULTIPLYING LYMPHOCYTES

BACKGROUND OF THE INVENTION

1. Field of the Invention

The invention concerns a process for producing and multiplying lymphocytes as well as a composition which is suitable as a culture medium for lymphocytes.

2. Description of the Related Art

The production and multiplication of lymphocytes is problematic. Some types of lymphocytes cannot be cultured at all in vitro or are very difficult to culture in vitro. Native B lymphocytes can for example only be cultured for a short period and T lymphocytes require difficult culture conditions for longer culture such as a combination of growth factor(s) and "feeder cells" ("nurse cells") or the use of unphysiological and potentially dangerous substances such as tumour promoters (phorbol esters) in combination with ionophoric substances (e.g. ionomycin) or plant lectins (e.g. phytohaemagglutin, PHA). This puts severe constraints on possibilities for the long-term culture and multiplication of T lymphocytes and other lymphocytes, and the production of lymphocytes in significant amounts for diagnostic or therapeutic purposes is very limited or impossible.

However, there is manifold interest in the ability to produce, culture and multiply lymphocytes in vitro e.g. B lymphocytes as producers of specific antibodies or cytotoxic T lymphocytes (CTL) to treat infections or tumours, in addition regulator T lymphocytes (helper or suppressor T lymphocytes) for the diagnosis and treatment of autoimmune diseases or "natural killer (NK) lymphocytes for treating malignant growths.

Hybridoma cells which are formed from a fusion of B lymphocytes or T lymphocytes with malignant, lympoid cells (e.g. myeloma cells) can be cultured and multiplied without difficulty. Such hybridoma cells have the immunological function of the original lymphocytes as well as the essentially unlimited ability to proliferate of the malignant fusion partner. However, the application of the hybridoma technique is limited to a few animal species (mouse, rat) and essentially fails in other mammalian species and also in particular in humans.

A process for the production of proliferating CD4+ lymphocytes is described in WO90/10059. According to this peripheral mononuclear blood cells (PBNMC) are treated with alkyl esters to remove monocytes and granulocytes and subsequently cultured in a culture medium which contains a T cell stimulant and/or IL-2. Mitogens such as PHA are used as the T cell stimulant. However, the use of IL-2 alone only leads to a low proliferation of the cells. The addition of mitogenic substances during the culture of cells which are subsequently to be implanted into a patient is critical.

A process for the culture of T cells in the presence of interleukin-2 is also described in EP-A 0 203 403. A disadvantage of this process is also that the T cells can only be proliferated to a slight extent by this means.

A process for culturing and multiplying tumoricidal T lymphocytes is described in WO94/23014 by co-culturing lymphocytes with a cell line (stimulator cells) while avoiding an allogenic stimulation and without addition of interleukin-2. In this process resting T lymphocytes are activated to effector cells which recognize and kill tumour cells or inhibit their growth. A considerable amount of fermentation is required to provide such stimulator cells for the mass proliferation of for example tumoricidal killer T cells. In addition the killer T cells must be separated in a sterile manner from these stimulator cells or their cell debris before use (reinfusion into the patient).

V. Kutnik et al., Period. Biol. 92 (1990) 48 describe that, in the allogenic mixed lymphocyte reaction of mouse spleen lymphocytes, the addition of IL2 restores the cyclosporin A-induced inhibition of the proliferation of the responder cells and increases their alloreactivity.

Pierson, B. A. et al., Blood 87 (1996) 180–189 describe that isolated human NK cells (CD56+, CD3−) can be multiplied to a slight extent in culture by adding IL2. The addition of supernatants of irradiated mononuclear cells from blood increases the multiplication of the NK cells. Thrombospondin was identified as the active principle of this effect which does not act directly but rather indirectly by activation of latent TGFβ. TGFβ activated in this manner inhibits the proliferation in the early phase of the culture and increases the further proliferation. A repeated addition of TGFβ when the medium is changed inhibits the growth of the cells and in this case suppresses the proliferation of the NK cells. In Immunological Invest. 25 (1996) 129–151 I. A. Ayoub investigates the effect of human TGFβ on a bovine CD4+ lymphoblastoid T cell line (BLTC) which grows autonomously in IL2-containing medium. The cell line is arrested in medium without IL2. The addition of TGFβ to the arrested BLTC drives them rapidly into apoptosis. The simultaneous addition of IL2 abolishes the arrest and prevents the induction of apoptosis. The addition of TGFβ to suboptimal concentrations of IL2 co-stimulates the proliferation of the BLTC.

In Intern. Immunol. 6 (1994) 631–638 R. de Jong describes the effect of TGFβ1 on the proliferation of isolated subpopulations of human CD4+ T lymphocytes. TGFβ1 amplifies the proliferation of CD4 cells (CD45 RA+) by antibodies in the presence of IL2, but the proliferation of pre-activated T cells (CD45 RO+) is inhibited by the addition of TGFβ1. However, it turned out that the induced proliferation of the CD45 RA+ cells is inhibited after five days by addition of TGFβ1.

A. Cerwenka describes in J. Immunol. 156 (1996) 459–464 that the presence of TGFβ1 during the primary stimulation of human T lymphocytes increases their ability to survive in secondary cultures and reduces their susceptibility to apoptosis-inducing anti-Fas antibodies. The addition of TGFβ1 also reduces the apoptosis susceptibility of primary activated T lymphocytes to secondary activation. A survival of the T cells over a long period is ensured in the presence of IL2 and TGFβ1.

T. H. Inne et al., J. Immunol. 148 (1992) 3847–3856 describe that the proliferation of CTLL-2 cells (murine T cell line) in IL2-containing medium is inhibited by addition of TGFβ1. In addition to the inhibition of proliferation, TGFβ1 induces a change in the cell morphology and induces the expression of the surface molecule CD8 in CTLL-2. A combination of IL2 and TGFβ also induces an increased expression of CD8 in murine thymocytes which have been activated by phorbol dibutyrate and ionomycin. In this case the addition of TGFβ1 also reduces the proliferation rate.

However, TGFβ is not a substance that is readily and cheaply available in adequate amounts. TGFβ is usually either isolated from natural sources or produced recombinantly. The main object of the invention was to provide an effective and cheap means for culturing and multiplying lymphocytes as well as a process for the production of pancytotoxic T cells. A further object of the present invention is to provide a process which enables lymphocytes to be produced, cultured and/or multiplied in a simple manner on a large scale.

SUMMARY OF THE INVENTION

The subject matter of the invention is a process for culturing and/or multiplying lymphocytes in a cell culture medium which contains a lymphocyte growth factor and additionally aurintricarboxylic acid, cyclosporin and/or ascomycin.

Surprisingly the process according to the invention enables lymphocytes with special properties to be produced in a simple manner, to be cultured over a long period and to be multiplied on a considerable scale. The process according to the invention is particularly suitable for culturing and multiplying T lymphocytes and NK lymphocytes.

Furthermore it has turned out that the process according to the invention particularly advantageously enables lymphocytes to be cultured over a long period (more than 14 days) and to be multiplied on a large scale (factor of 100, 1000 or more). In addition a combination of a lymphocyte growth factor and additionally aurintricarboxylic acid, cyclosporin and/or ascomycin enables pancytotoxic T cells to be multiplied from lymphocyte mixtures by long-term culture, preferably from a lymphocyte cell population and hence enables such cells to be produced simply and in large amounts.

A lymphocyte growth factor is understood as a substance which is able to promote cell division of lymphocytes. Lymphocyte growth factors are known to a large extent to a person skilled in the art. Suitable T lymphocyte growth factors are for example interleukin 1 (IL-2) and interleukin 15 (IL-15). A suitable NK lymphocyte growth factor is e.g. IL-15. Suitable B lymphocyte growth factors are for example interleukin 13 (IL-13), IL-14 and IL-10 (Callard, R. E., and Gearing, J. H., The Cytokine Facts Book, Academic Press, London, 1994).

Surprisingly ciclosporin (e.g Cyclosporin A®), ascomycin (FK520) and/or tacrolimus (FK506) can be used according to the invention to increase proliferation. These are substances which bind to a cyclophilin and inhibit calcineurin in this complex. Other substances which have these properties are also suitable according to the invention. Pazderka-F., et al., Transpl. Immunol. (1996) 23–31, Rusnak-F., et al., Bone-Marrow-Transplant 17 (1996) 309–13, Su-Q., et al., Ren-Physiol-Biochem. 18 (1995) 128–39, Baughman-G., et al., Mol-Cell-Biol. 15 (1995) 4395–402, Kawamura, A., et al., J-Biol-Chem. 270 (1995) 15463–6, Kakalis, L T., et al., FEBS-Lett. 362 (1995) 55–8.

Surprisingly aurintricarboxylic acid (ATA) can also be used to increase the proliferation of lymphocytes. Aurintricarboxylic acid is a substance which inhibits the interaction of proteins and nucleic acids [Gonzales, R. G. et al.: Biochemistry 19: 4299–4303 (1980)] and is a general inhibitor of nucleases.

The amount of aurintricarboxylic acid which is added in the process according to the invention can also be varied and is to a certain extent dependent on the medium used and on the cell to be cultured. It has turned out that for example when culturing tumour-infiltrating lymphocytes (TIL) in serum-containing medium it is advantageous to add 0.1–100 μM ATA.

Lymphocytes within the sense of the invention are understood as leucocytes which are derived from lymphocyte progenitor cells in the haematopoietic system and can be for example found in blood, in the lymph, in the spleen, in lymph nodes, in tumours (tumour-infiltrating lymphocytes, TIL) or inflamed tissue. Important subgroups are T lymphocytes, NK lymphocytes and B lymphocytes. B lymphocytes are antibody-producing lymphocytes in their mature form.

T lymphocytes (T cells) are understood as lymphocytes which are for example involved in cell-mediated cytotoxicity, in allergy of the delayed type and in the activation of B lymphocytes. There are numerous different types (subtypes) of T cells which can be each distinguished by their function and/or their cell surface antigens (see e.g. Imm. Rev. (1993), 74 and (1992), 82; Advances in Immunology 58 (1995) 87). Such surface antigens are for example referred to as CD (Cluster of Differentiation) antigens. The expression of the antigen-recognizing T cell receptor is typical for all T cells. T cells develop from haematopoietic stem cells and mature, with some exceptions, in the thymus. Examples of T cells are cytotoxic T cells, helper T cells, suppressor T cells, suppressor-inducer T cells and killer T cells.

Natural killer cells (NK cells) are lymphoid cells which develop from haematopoietic stem cells and differ from T cells and B cells in that they express neither the T cell receptor nor the B cell receptor and are CD3–.

DETAILED DESCRIPTION OF THE INVENTION

The culture of lymphocytes in the process according to the invention is carried out in a conventional basic culture medium which additionally contains a lymphocyte growth factor and cyclosporin and/or ascomycin. All media are suitable as basic culture media which are usually used to culture mammalian cells. Such culture media can either contain serum or be serum-free and are known to any person skilled in the art. Examples are RPMI 1640-medium, Dulbecco's Modified Eagles Medium (DMEM), F12 medium or a mixture of the latter (DF medium) which can be used in a serum-containing and also in a serum-free form. If serum-free media are used, the medium must be supplemented by critical components. Such critical components are, as known to any person skilled in the art, albumin, transferrin, selenite and insulin. Serum-free media which already contain all critical supplements such as e.g. the culture medium X-Vivo 20® (Bio-Whittaker, Serva) are also particularly suitable.

The amounts of lymphocyte growth factor and cyclosporin and/or ascomycin which are added in the process according to the invention can vary and, to a certain extent, depend on the medium used (serum-free or serum-containing) and on the cell to be cultured. It has turned out that in serum-free culture amounts of $0.1-10 \times 10^{-9}$ mol/l growth factor and $10^{-10}-10^{-2}$ mol/l cyclosporin and/or ascomycin are suitable. Consequently in the culture of T cells and/or NK cells in serum-free medium it is advantageous to for example add 10–20 ng/ml IL-2 or IL-15 and 5–20 ng/ml Cyclosporin-A® and/or 1–10 ng/ml Ascomycin®.

The process according to the invention is especially suitable for culturing and multiplying killer T cells (KT cells) and tumoricidal killer T cells. Such tumoricidal killer T cells can for example be produced according to WO 94/23014 by co-culturing lymphocytes, which for example have been isolated from blood, with stimulator cells. In this process resting T lymphocytes are activated to effector cells which recognize and kill tumour cells and inhibit their growth. The activated T lymphocytes are stimulated to proliferate in this co-culture and can be further cultured and multiplied by the process according to the invention.

The process according to the invention is also advantageous for the production and multiplication of pancytotoxic T cells. A combination of a lymphocyte growth factor with aurintricarboxylic acid, and a substance which binds to cyclophilin and inhibits calcineurin in this complex, or an apoptosis antagonist is suitable. In addition the process according to the invention enables the sustained proliferation of blood lymphocytes after treatment with leucyl-leucine-methyl ester. The phenotyping of such cells produced according to the invention on the basis of surface markers shows that the proliferating cells are uniformly T lymphocytes (100% CD3+). These cells exhibit a previously unknown activity which is referred to as pancytotoxic activity in the following. Pancytotoxic T cells are characterized in that they indiscriminately kill normal cells such as e.g. fibroblasts, keratinocytes or endothelial cells and also tumour cells such as e.g. malignant melanoma, T lymphoma or lung carcinoma. Surprisingly pancytotoxic T cells can be produced from mononuclear cells by treatment with a combination IL-2 and apoptosis antagonists. Pancytotoxic T cells can be used advantageously for the local treatment of tumours (e.g. tumour metastases).

An apoptosis antagonist (apoptosis inhibitor) is to be understood as a substance which is able to not allow the genetically determined self-destruction program to become effective in a cell that would lead to cell death after activation, and which partially or completely slows or prevents the lysis of a cell after activation of a suicide signal. Suitable substances are for example described in Kroemer, G., Advances in Immunology 58 (1995) 211–296. According to the invention substances are suitable which are able to inhibit agents with an apoptosis signal effect on lymphocytes (e.g. an antibody to TNFα which prevents binding of this cytokine to its receptor). Furthermore substances are suitable which prevent reception of an apoptosis signal by the lymphocytes (e.g antibody to the TNFα receptor which inhibits binding of TNFα to this receptor). Substances are also suitable which are able to prevent apoptosis by interrupting the signal chain from the cell membrane into the inside of a lymphocyte (e.g. an inhibitor of sphingomyelinase, inhibition of the formation of ceramide). Finally an apoptosis inhibitor is also to be understood as a substance which is able to activate the anti-apoptosis program in a lymphocyte which is also genetically determined (e.g. up-regulation of the bcl-2 expression). Cyclosporin and ascomycin are also suitable as calcineurin inhibitors.

It has surprisingly turned out that when mononuclear blood cells (PBMNC) are cultured without pre-treatment with leucyl-leucine-methyl ester, lymphocytes usually grow after a latency period of 14–28 days which can be multiplied as desired. Phenotyping of these cells shows that they represent a mixture of T cells (CD2+, CD3+) and NK cells (CD2+, CD3−, CD16+). Functionally they are also pancytotoxic and thus differ from KT cells. In this case it is also preferable to use IL2 or IL15 as a lymphocyte growth factor and Cyclosporin or Ascomycin.

The following examples, publications and the figures further elucidate the invention, the scope of which results from the patent claims. The described processes are to be understood as examples but still describe the subject matter of the invention even after modifications.

EXAMPLE 1
Production of Killer T Cells

Mononuclear cells from peripheral blood (PBMNC) of human donors are isolated by means of gradient centrifugation (lymphocyte separation medium, BM), washed twice with phosphate-buffered saline solution and incubated at a density of $5-10\times10^6$ cells/ml DF medium according to Thiele and Lipsky (J. Immunol. 136 (1986) 1038–1048) with 250 µM leucyl-leucine-methyl ester (BM) for 20 minutes at room temperature. After washing with DF medium the cells are cultured at 37° C. in 8% $CO_2$ atmosphere at a density of $1-2\times10^6$ per ml DF medium together with irradiated (2000 rad) HB654 cells or HB617 cells (stimulator cells; $2-5\times10^5$ per ml). On day 5–6 of the co-culture half to two thirds of the culture medium is renewed and irradiated stimulator cells ($2-5\times10^5$ per ml) are added again. From day 8–10 after starting the co-culture, when all stimulator cells have been destroyed by the cytotoxic activity of the killer T cells, the killer T cells are used for the following examples.

Phenotyping the cells on day 10 of the co-culture shows that >95% of the cells are CD3+, ca. 40% CD4+ and ca. 60% CD8+. Cells with the markers CD19 or CD16 are not found.

EXAMPLE 2
Multiplication of Killer T Cells in Serum-free Medium which Contains Interleukin-2 (IL-2) and Cyclosporin A (CsA).

Killer T cells which have been produced according to example 1 are washed once in DF medium and cultured at a density of $5\times10^5$ per ml DF medium in two separate preparations that are denoted A and B. Human recombinant IL-2 (BM; 20 ng/ml) and CsA (Sandoz; 12.5 ng/ml) are added to preparation A. Only CsA (12.5 ng/ml) is added to preparation B. Half of the culture medium is renewed every second day and the cell count is adjusted to $5\times10^5$ per ml.

Figure 1:
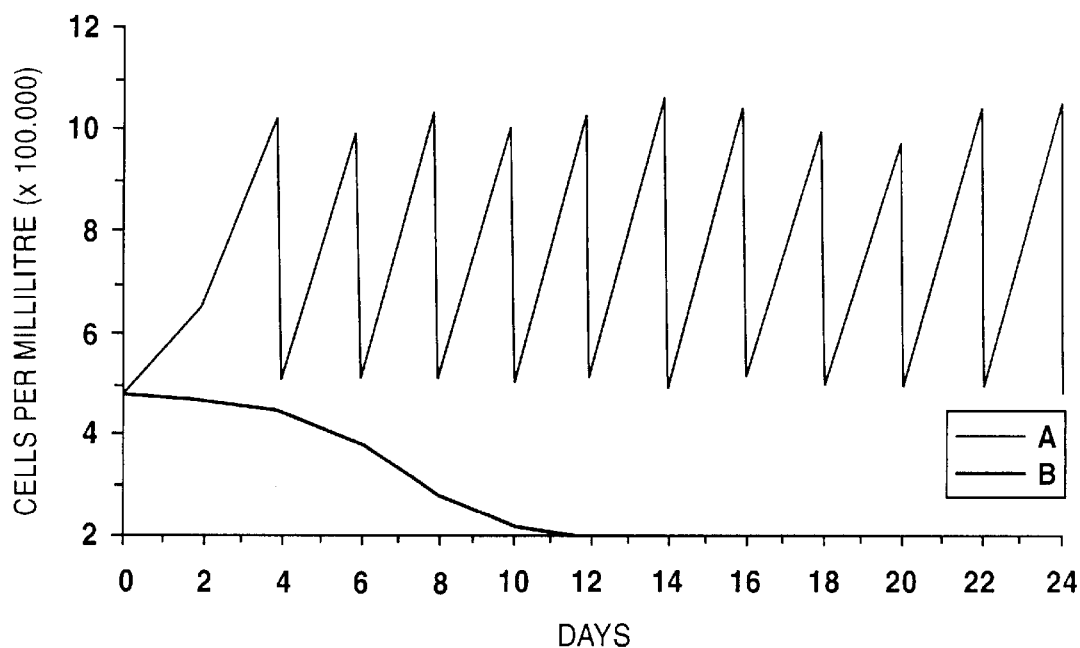
FIG. 1 shows the growth behaviour of killer T cells in serum-free DF medium on addition of IL-2+CsA(A) and CsA alone (B).

As shown in FIG. 1 the killer T cells multiply in preparation A (IL-2+ CsA) with a doubling time of about 48 hours for at least ten doubling cycles (corresponds to 1000-fold multiplication). In preparation B (only CsA) the killer T cells do not multiply.

EXAMPLE 3
Multiplication of Killer T Cells in Serum-free Medium which Contains Interleukin-15 (IL-15) and Cyclosporin A (CsA).

Killer T cells which have been produced according to example 1 are washed once in DF medium and cultured at a density of $5\times10^5$ per ml DF medium in two separate preparations that are denoted A and B. Human recombinant IL-15 (R & D Systems; 15 ng/ml) and CsA (Sandoz; 12.5 ng/ml) are added to preparation A. Only IL-15 (15 ng/ml) is added to preparation B. Half of the culture medium is renewed every second day and the cell count is adjusted to $5\times10^5$ per ml.

Figure 2:
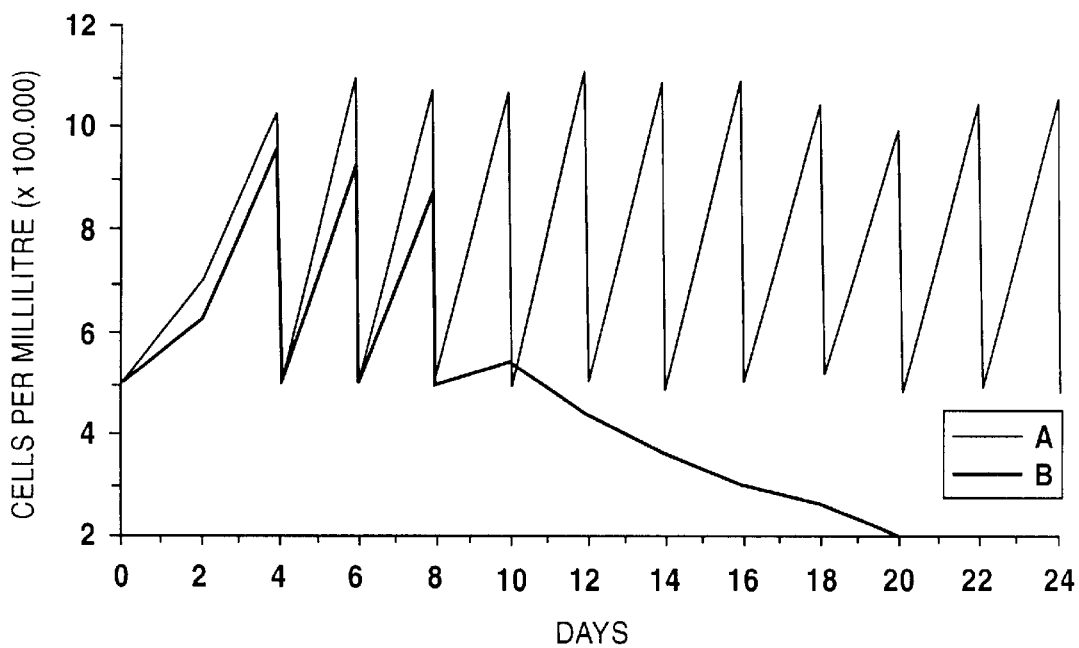
FIG. 2 shows the growth behaviour of killer T cells in serum-free DF medium on addition of IL-15 and CsA(A) and IL-15 alone (B).

As shown in FIG. 2 the killer T cells multiply in preparation A (IL-15+CsA) with a doubling time of about 48 hours for at least 11 doubling cycles. In preparation B (only IL-15) the proliferation stagnates after 3 doubling cycles.

EXAMPLE 4
Multiplication of Killer T Cells in Serum-free Medium Containing Interleukin-2 (IL-2) and Ascomycin (FK 520).

Killer T cells which have been produced according to example 1 are washed once in DF medium and cultured at a density of $5\times10^5$ per ml DF medium in two separate preparations that are denoted A and B. rh IL-2 (20 ng/ml) and Ascomycin (Calbiochem; 2.5 ng/ml) are added to preparation A. Only Ascomycin (2.5 ng/ml) is added to preparation B. Half of the culture medium is renewed every second day and the cell count is adjusted to $5\times10^5$ per ml.

Figure 3:
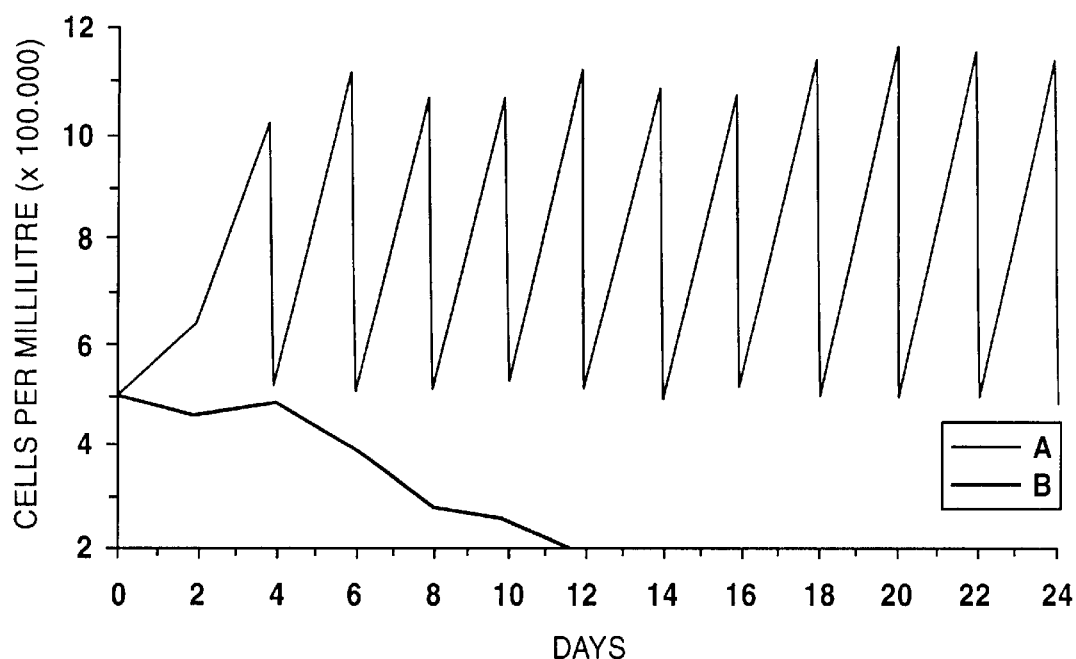
FIG. 3 shows the growth behaviour of killer T cells in serum-free DF medium on addition of IL-2 and Ascomycin (FK520) (A) and Ascomycin alone (B).

As shown in FIG. 3 the killer T cells multiply in preparation A (IL-2+Ascomycin) with a doubling time of about 48 hours for at least ten doubling cycles. In preparation B (only Ascomycin) no multiplication of killer T cells is observed.

EXAMPLE 5
Multiplication of NK and T Lymphocytes from Mononuclear Cells of Human Blood in Serum-free Medium Which Contains Interleukin-2 (IL-2) and Transforming Growth Factor-β1 (TGF-β1).

Mononuclear cells from peripheral blood (PBMNC) of a human donor are isolated by means of gradient centrifugation (lymphocyte separation medium, Boehringer Mannheim GmbH, Germany (BM)), washed twice with phosphate-buffered saline solution and taken up in DF medium at a density of $1\times10^6$ cells/ml and cultured in three separate preparations which are denoted A, B and C. Recombinant human IL-2 (BM, 20 ng/ml) and rh TGFβ1 (BM, 4 ng/ml) are added to preparation A, only IL-2 (20 ng/ml) is added to preparation B and only TGFβ1 (4 ng/ml) is added to preparation C. Half of the culture medium (+cytokine(s)) is renewed every second day and the cell count is adjusted to ca. $1\times10^6$ cells/ml during the first 7 days and subsequently to ca. $0.5\times10^5$ cells/ml.

In preparation A (IL-2+TGFβ1) the number of non-adherent lymphoid cells increases approximately from day 5 after the beginning of the culture, firstly with a doubling time of ca. 96 hours, from day 20 when no more colonies with adherent monocytic cells are detectable with a doubling time of less than 48 hours. On day 50 of the continuous culture the cell count has increased more than $10^4$-fold compared to the initial state. The analysis of the cells with regard to their surface markers yields the following result on day 50: the population contains:

ca. 50% NK cells (CD2+, CD3−, CD16+, CD56+) and ca. 50% T cells (CD3+, CD4+, CD8+)

In preparation B (only IL-2) lymphoid cells only multiply moderately (<50-fold) over ca. 16 days, then stagnate and die after ca. 20 further days.

In preparation B (only TGFβ1) the cells do not multiply.

EXAMPLE 6
Multiplication of Killer T Cells in Serum-free Medium Containing Interleukin 2 (IL-2) and Aurintricarboxylic Acid (ATA).

Killer T cells which have been produced according to example 1 are washed once in DF medium and cultured at a density of $5\times10^5$ per ml DF medium in two separate preparations that are denoted A and B. IL-2 (20 ng/ml) and aurintricarboxylic acid (Aldrich Chemie; 4.2 μg/ml) are added to preparation A. Only aurintricarboxylic acid (4.2 μg/ml) is added to preparation B. Half of the culture medium is renewed every third day and the cell count is adjusted to $5\times10^5$ per ml.

Figure 4:
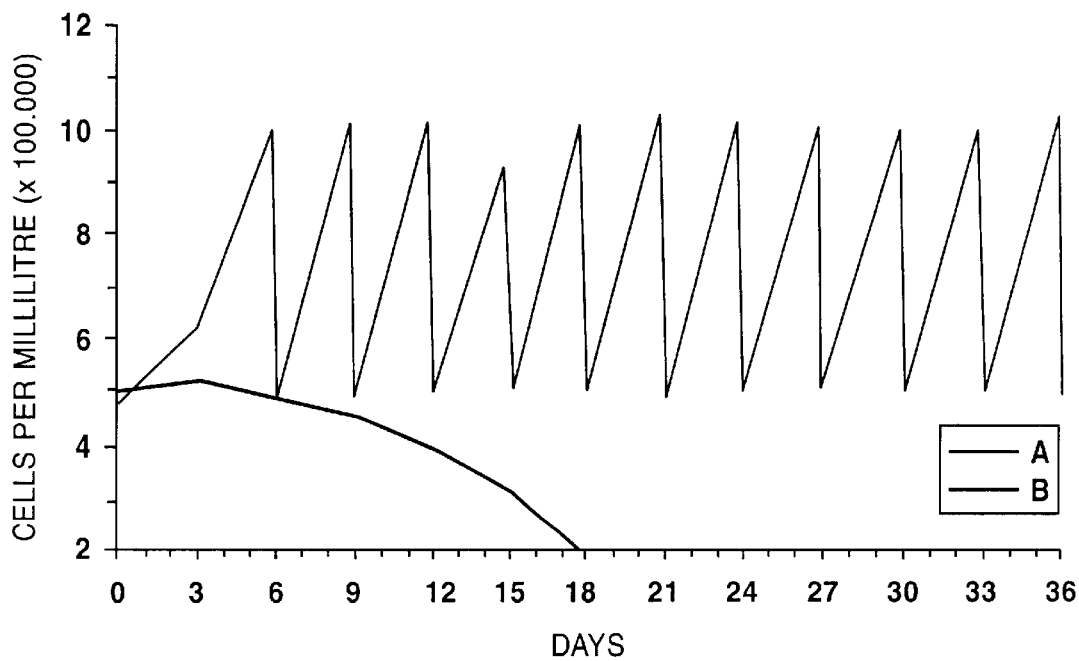
FIG. 4 shows the growth behaviour of killer T cells in serum-free DF medium on addition of IL-2 and aurintricarboxylic acid (A) and arintricarboxylic acid alone (B).

As shown in FIG. 4 the killer T cells multiply in preparation A (IL-2+ATA) with a doubling time of about 72 hours for at least 11 doubling cycles. In preparation B (only ATA) the killer T cells do not multiply.

EXAMPLE 7
Multiplication of Tumour-infiltrating Lymphocytes in a Medium which Contains Interleukin-2 (IL-2) and Aurintricarboxylic Acid (ATA).

The nodules of a human colon carcinoma which was removed by an operation from the large intestine is freed of connective tissue and normal parts of the intestine and cut into ca. 2×2×3 mm pieces. The tumour fragments are taken up in Iscove-modified DME medium (Gibco) which contains 15% FCS (BM) and divided equally into four culture dishes which are named A, B, C and D. IL-2 (20 ng/ml) is added to preparation A, aurintricarboxylic acid (4.2 μg/ml) is added to preparation B and IL-2 (20 ng/ml) plus aurintricarboxylic acid (4.2 μg/ml) is added to preparation C. Preparation D remains without additions. Three quarters of the respective culture media is removed each second day without changing the tissue or cell content. Microscopic control of the cultures shows that after 24–48 hours lymphocytic cells migrated out of the tumour tissue fragments which multiplied in the partial culture C which contains IL-2 plus ATA but not in the partial cultures A, B or D. After a ten day culture the picture is as follows: In A and B (only IL-2 or ATA) the number of emigrated lymphocytes has remained constant compared to day 2, in D (no additives) hardly any lymphocytes are detectable. In the partial culture C the number of lymphocytes has increased 20-fold compared to A or B. The lymphocytes from C are isolated from the partial culture C and they are analysed on the basis of their surface markers. The population contains:

ca. 60% T lymphocytes (CD3+, CD4+, CD8+, CD19−)

ca. 25% NK cells (CD2+, CD3−, CD56+, CD19−) and ca. 15% B lymphocytes (CD19+, CD3−).

LIST OF REFERENCE

Advances in Immunology 58 (1995) 87
Ayoub, I. A., Immunological Invest. 25 (1996) 129–151
Baughman-G., et al., Mol-Cell-Biol. 15 (1995) 4395–402
Callard, R. E., and Gearing, J. H., The Cytokine Facts Book, Academic Press, London 1994
Cerwenka, A. J. Immunol. 156 (1996) 459–464
EP-A 0 203 403
Immm. Rev. (1992) 82
Imm. Rev. (1993) 74
Inne, T. H., et al., J. Immunol. 148 (1992) 3847–3856
Jong de, R., Intern. Immunol. 6 (1994) 631–638
Kakalis, L. T., et al., FEBS-Lett. 362 (1995) 55–8
Kawamura, A., et al., J-Biol-Chem. 270 (1995) 15463–6
Kroemer, G., Advances in Immunology 58 (1995) 211–296
Kutnik, V., et al., Period. Biol. 92 (1990) 48
Pazderka-F., et al., Transpl-Immunol. (1996) 23–31
Pierson, B. A. et al., Blood 87 (1996) 180–189
Rusnak-F., et al., Bone-Marrow-Transplant. 17 (1996) 309–13
Su-Q., et al., Ren-Physiol-Biochem. 18 (1995) 128–39
Thiele and Lipsky, J. Immunol. 136 (1986) 1038–1048
WO90/10059
WO94/23014
Gonzales, R. G. et al., Biochemistry 19: 4299–4303 (1980)

What is claimed is:

1. A method for the multiplication of lymphocytes in a lymphocyte cell culture, comprising incubating lymphocytes in a suitable cell culture medium which contains, from the beginning of incubation, both a compound selected from group A consisting of IL-2, IL-10, IL-13, IL-14 and IL-15, and, simultaneously, a compound selected from group B consisting of cyclosporine, ascomycin (FK520), tacrolimus (FK506), and aurintricarboxylic acid, wherein said compound of group A and said compound of group B are present in the cell culture medium at a concentration effective for allowing the cells to multiply, and carrying out incubation for at least 10 days, wherein a partial volume of said cell culture medium containing both the group A an the group B compound is renewed during said incubation of at least 10 days.

2. The method of claim 1, wherein renewal of a volume of the cell culture medium containing both the group A and the Group B compound is carried out repeatedly and in equal intervals during said incubation of at least 10 days.

3. The method of claim 2, wherein after each renewal of cell culture medium the cell culture is adjusted to a cell concentration equal to the one at the beginning of said incubation of at least 10 days.

4. The method of claim 1, wherein incubation is carried out until a number of at least 10 doubling cycles is reached.

5. The method of claim 1, wherein the lymphocytes provided in said cell culture medium are selected from the group consisting of peripheral blood mononuclear cells, killer T cells, tumoricidal killer T cells, tumor-infiltrating lymphocytes, NK cells and B lymphocytes.

6. The method of claim 1, wherein the cell culture medium is serum-free and contains $0.1$–$10 \times 10^{-9}$ mol/l of interleukin 2 or interleukin 15, as the group A compound, together with $10^{-10}$–$10^{-2}$ mol/l of the group B compound being either cyclosporin or ascomycin or mixture of cyclosporin and ascomycin.

7. The method of claim 1, wherein the cell culture medium contains fetal calf serum (FCS) and wherein the group B compound is aurintricarboxylic acid which is present in the cell culture medium at a concentration of $0.1$–$100$ $\mu$mol/l.

* * * * *